US010429399B2

(12) United States Patent
Boyden

(10) Patent No.: US 10,429,399 B2
(45) Date of Patent: Oct. 1, 2019

(54) PROCESS CONTROL FOR INCREASED ROBUSTNESS OF GENETIC ASSAYS

(71) Applicant: Good Start Genetics, Inc., Cambridge, MA (US)

(72) Inventor: Eric D. Boyden, Cambridge, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 0 days.

(21) Appl. No.: 14/858,637

(22) Filed: Sep. 18, 2015

(65) Prior Publication Data

US 2016/0084854 A1 Mar. 24, 2016

Related U.S. Application Data

(60) Provisional application No. 62/054,725, filed on Sep. 24, 2014.

(51) Int. Cl.
*G01N 33/84* (2006.01)
*C12N 15/10* (2006.01)
*G01N 21/80* (2006.01)
*G01N 1/30* (2006.01)
*G01N 33/68* (2006.01)
*C12Q 1/6806* (2018.01)
*G01N 31/22* (2006.01)

(52) U.S. Cl.
CPC ......... *G01N 33/84* (2013.01); *C12N 15/1003* (2013.01); *G01N 1/30* (2013.01); *G01N 21/80* (2013.01); *G01N 33/689* (2013.01); *C12Q 1/6806* (2013.01); *G01N 31/221* (2013.01)

(58) Field of Classification Search
None
See application file for complete search history.

(56) References Cited

U.S. PATENT DOCUMENTS

| | | |
|---|---|---|
| 4,149,852 A | 4/1979 | Tiru et al. |
| 4,683,195 A | 7/1987 | Mullis et al. |
| 4,683,202 A | 7/1987 | Mullis |
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,342,328 A | 8/1994 | Grossman et al. |
| 5,348,853 A | 9/1994 | Wang et al. |
| 5,459,307 A | 10/1995 | Klotz, Jr. |
| 5,486,686 A | 1/1996 | Zdybel, Jr. et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,766,875 A * | 6/1998 | Hafeman ............. G01N 21/253 356/4.01 |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,971,921 A | 10/1999 | Timbel |
| 5,993,611 A | 11/1999 | Moroney, III et al. |
| 5,994,056 A | 11/1999 | Higuchi |
| 6,033,854 A | 3/2000 | Kumit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |
| 6,179,819 B1 | 1/2001 | Haswell |
| 6,197,508 B1 | 3/2001 | Stanley |
| 6,197,574 B1 * | 3/2001 | Miyamoto ............. C12M 23/06 435/287.6 |

(Continued)

FOREIGN PATENT DOCUMENTS

| | | |
|---|---|---|
| EP | 1 321 477 A1 | 6/2003 |
| EP | 1 564 306 A2 | 8/2005 |

(Continued)

OTHER PUBLICATIONS

Heger et al., J. Phys. Chem. B, 110:1277-1287 (2006).*
International Search Report and Written Opinion dated Jan. 22, 2016, for International Patent Application No. PCT/US2015/050964, filed Sep. 18, 2015 (6 pages).
Kneen, 1998, "Green fluorescent protein as a noninvasive intracellular pH indicator," Biophys J. 74(3): 1591-99.
Llopis, 1998, "Measurement of cytosolic, mitochondrial, and Golgi pH in single living cells with green fluorescent proteins," Proc. Natl. Acad. Sci. U.S.A. 95(12):6803-08.
Miesenbock, 1998, "Visualizing secretion and synaptic transmission with pH-sensitive green fluorescent proteins," Nature 394(6689): 192-95.

(Continued)

*Primary Examiner* — Thomas J. Visone
(74) *Attorney, Agent, or Firm* — Brown Rudnick LLP; Thomas C. Meyers

(57) ABSTRACT

The present disclosure describes a method of processing a biological sample. The method includes contacting the sample with a pH indicator that changes color in response to changes in pH. The presence of a pH indicator such as cresol red provides the benefit of improved visualization of the sample, verification that the sample is properly frozen and thawed, and increased precision in pH adjustments during the assay, among other benefits.

7 Claims, 4 Drawing Sheets

(56) References Cited

U.S. PATENT DOCUMENTS

| | | |
|---|---|---|
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,335,200 B1 | 1/2002 | Tiru et al. |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vemachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0091666 A1 | 7/2002 | Rice et al. |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1* | 2/2004 | Robbins, Jr. ............ C12M 27/12 435/291.6 |
| 2004/0106112 A1 | 6/2004 | Nilsson et al. |
| 2004/0142325 A1 | 7/2004 | Mintz et al. |
| 2004/0152108 A1 | 8/2004 | Keith et al. |
| 2004/0170965 A1* | 9/2004 | Scholl ................. C12N 5/0688 435/5 |
| 2004/0171051 A1 | 9/2004 | Holloway |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0272065 A1 | 12/2005 | Lakey et al. |
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0149047 A1* | 7/2006 | Nanduri ................. C12N 9/78 536/23.2 |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092863 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0225487 A1 | 9/2007 | Nilsson et al. |
| 2007/0238122 A1 | 10/2007 | Allbritton et al. |

(56) References Cited

U.S. PATENT DOCUMENTS

| | | |
|---|---|---|
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0013911 A1* | 1/2012 | Ruschin .......... G01N 21/77 356/451 |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268474 A1 | 10/2013 | Nizzari et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0178445 A1 | 6/2015 | Cibulskis et al. |
| 2015/0299767 A1 | 10/2015 | Armour et al. |
| 2016/0034638 A1 | 2/2016 | Spence et al. |
| 2016/0210486 A1 | 7/2016 | Porreca et al. |
| 2017/0044610 A1 | 2/2017 | Johnson |
| 2017/0129964 A1 | 5/2017 | Cheung |

FOREIGN PATENT DOCUMENTS

| | | |
|---|---|---|
| EP | 10770071.8 | 11/2010 |
| EP | 2425240 A2 | 3/2012 |
| EP | 2 437 191 A2 | 4/2012 |
| EP | 2716766 A1 | 4/2014 |
| WO | 95/011995 A1 | 5/1995 |
| WO | 96/019586 A1 | 6/1996 |
| WO | 98/014275 A1 | 4/1998 |
| WO | 98/044151 A1 | 10/1998 |
| WO | 99/64832 A1 | 12/1999 |
| WO | 00/018957 A1 | 4/2000 |
| WO | 02/093453 A2 | 11/2002 |
| WO | 2004015609 A2 | 2/2004 |
| WO | 2004018497 A2 | 3/2004 |
| WO | 2004/083819 A2 | 9/2004 |
| WO | 2005/003304 A2 | 1/2005 |
| WO | 2005/079531 A2 | 9/2005 |
| WO | 2007/010251 A2 | 1/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2008/093329 A2 | 8/2008 |
| WO | 2009/036525 A2 | 3/2009 |
| WO | 2010/024894 A1 | 3/2010 |
| WO | 2010/126614 A2 | 11/2010 |
| WO | 2011/006020 A1 | 1/2011 |
| WO | 2011/102998 A2 | 8/2011 |
| WO | 2012/006291 A2 | 1/2012 |

(56) References Cited

FOREIGN PATENT DOCUMENTS

| | | |
|---|---|---|
| WO | 2012/040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2012/149171 A1 | 11/2012 |
| WO | 2012/170725 A2 | 12/2012 |
| WO | 2013/052557 A2 | 4/2013 |
| WO | 2013/058907 A1 | 4/2013 |
| WO | 2013/148496 A1 | 10/2013 |
| WO | 2013/164424 A1 | 11/2013 |
| WO | 2013/177086 A1 | 11/2013 |
| WO | 2013/191775 A2 | 12/2013 |
| WO | 2014/074246 A1 | 5/2014 |
| WO | 2014/116881 A1 | 7/2014 |
| WO | 2015089333 A1 | 6/2015 |

OTHER PUBLICATIONS

Jones, 2008, Core signaling pathways in human pancreatic cancers revealed by global genomic analyses, Science 321(5897):1801-1806.

Kambara et al., Optimization of Parameters in a DNA Sequenator Using Fluorescence Detection, Nature Biotechnology 6:816-821 (1988).

Kennedy et al., 2013, Accessing more human genetic variation with short sequencing reads, American Society of Human Genetics 63rd Annual Meeting, Abstract, Oct. 22, 2013.

Kent, 2002, BLAT—The BLAST-like alignment tool, Genome Res 12(4): 656-664.

Kerem, 1989, Identification of the cystic fibrosis gene: genetic analysis, Science 245:1073-1080.

Kinde, 2012, FAST-SeqS: a simple an effective method for detection of aneuploidy by massively parallel sequencing, PLoS One 7(7):e41162.

Kircher, 2010, High-througput DNA sequencing—concepts and limitations, Bioassays 32:524-36.

Kirpekar, 1994, Matrix assisted laser desorption/ionization mass spectrometry of enzymatically synthesized RNA up to 150 kDa, Nucl Acids Res 22:3866-3870.

Klein, 2011, LOCAS—A low coverage sequence assembly tool for re-sequencing projects, PLoS One 6(8):e23455.

Koboldt, 2009, VarScan: variant detection in massively parallel sequencing of individual and pooled samples, Bioinformatics 25:2283-85.

Krawitz, 2010, Microindel detection in short-read sequence data, Bioinformatics 26(6):722-729.

Kreindler, 2010, Cystic fibrosis: exploiting its genetic basis in the hunt for new therapies, Pharmacol Ther 125(2):219-229.

Krishnakumar, 2008, A comprehensive assay for targeted multiplex amplification of human DNA sequences, PNAS 105:9296-301.

Kumar, 2010, Comparing de novo assemblers for 454 transcriptome data, Genomics 11:571.

Kurtz, 2004, Versatile and open software for comparing large genomes, Genome Biol 5:R12.

Lam, 2008, Compressed indexing and local alignment of DNA, Bioinformatics 24(6):791-97.

Langmead, 2009, Ultrafast and memory-efficient alignment of short DNA sequences to the human genome, Genome Biol 10:R25.

Larkin, 2007, Clustal W and Clustal X version 2.0, Bioinformatics, 23(21):2947-2948.

Lecompte, 2001, Multiple alignment of complete sequences (MACS) in the post-genomic era, Gene 270(1-2):17-30.

Li, 2003, DNA binding and cleavage by the periplasmic nuclease Vvn: a novel structure with a known active site, EMBO J 22(15):4014-4025.

Li, 2008, SOAP: short oligonucleotide alignment program, Bioinformatics 24(5):713-14.

Li, 2009, Fast and accurate short read alignment with Burrows-Wheeler transform, Bioinformatics, 25 (14):1754-60.

Li, 2009, SOAP2: an improved ultrafast tool for short read alignment, Bioinformatics 25(15):1966-67.

Li, 2009, The Sequence Alignment/Map format and SAMtools, Bioinformatics 25(16):2078-9.

Li, 2010, Fast and accurate long-read alignment with Burrows-Wheeler transform, Bioinformatics 26(5):589-95.

Li, 2011, Improving SNP discovery by base alignment quality, Bioinformatics 27:1157.

Li, 2011, Single nucleotide polymorphism genotyping and point mutation detection by ligation on microarrays, J Nanosci Nanotechnol 11(2):994-1003.

Li, 2012, A new approach to detecting low-level mutations in next-generation sequence data, Genome Biol 13:1-15.

Li, 2014, HUGO: Hierarchical mUlti-reference Genome cOmpression for aligned reads, JAMIA 21:363-373.

Lin, 2008, ZOOM! Zillions of Oligos Mapped, Bioinformatics 24:2431.

Lin, 2010, A molecular inversion prove assay for detecting alternative splicing, BMC Genomics 11(712):1-14.

Lin, 2012, Development and evaluation of a reverse dot blot assay for the simultaneous detection of common alpha and beta thalassemia in Chinese, Blood Cells Molecules, and Diseases 48(2):86-90.

Lipman, 1985, Rapid and sensitive protein similarity searches, Science 227(4693):1435-41.

Liu, 2012, Comparison of next-generation sequencing systems, J Biomed Biotech 2012:251364.

Ma, 2006, Application of real-time polymerase chain reaction (RT-PCR), J Am Soc 1-15.

MacArthur, 2014, Guidelines for investigating causality of sequence variants in human disease, Nature 508:469-76.

Maddalena, 2005, Technical standards and guidelines: molecular genetic testing for ultra-rare disorders, Genet Med 7:571-83.

Malewicz, 2010, Pregel: a system for large-scale graph processing, Proc. ACM SIGMOD Int Conf Mgmt Data 135-46.

Mamanova, 2010, Target-enrichment strategies for nextgeneration sequencing, Nature Methods 7(2):111-8.

Margulies, 2005, Genome sequencing in micro-fabricated high-density picotiter reactors, Nature, 437:376-380.

Marras, 1999, Multiplex detection of single-nucleotide variations using molecular beacons, Genetic Analysis: Biomolecular Engineering 14:151.

Maxam, 1977, A new method for sequencing DNA, PNAS, 74:560 564.

May, 1988, How Many Species Are There on Earth?, Science 241(4872):1441-9.

McDonnell, "Antisepsis, disinfection, and sterilization: types, action, and resistance," p. 239 (2007).

McKenna, 2010, The Genome Analysis Toolkit: a MapReduce framework for analyzing next-generation DNA sequencing data, Genome Res 20(9):1297-1303.

Meldgaard, 2004, Non-invasive method for sampling and extraction of mouse DNA for PCR, Laboratory Animals 38:413-17.

Meyer, 2007, Targeted high-throughput sequencing of tagged nucleic acid samples, Nucleic Acids Research 35(15):a97 (5 pages).

Meyer, 2008, Parallel tagged sequencing on the 454 platform, Nature Protocols 3(2):267-78.

Miller, 2010, Assembly algorithms for next-generation sequencing data, Genomics 95:315-327.

Mills, 2010, Mapping copy number variation by population-scale genome sequencing, Nature 470(7332):59-65.

Hodges, 2007, Genome-wide in situ exon capture for selective resequencing, Nat Genet 39(12):1522-7.

Holland, 2008, BioJava: an open-source framework for bioinformatics, Bioinformatics 24(18):2096-2097.

Homer et al., 2008, Resolving Individuals Contributing Trace Amounts of DNA to Highly Complex Mixtures Using High-Density SNP Genotyping Microarrays. PLoS One 4(8):e1000167.

Homer, 2009, BFAST: An alignment tool for large scale genome resequencing, PLoS ONE 4(11):e7767.

(56) References Cited

OTHER PUBLICATIONS

Housley, 2009, SNP discovery and haplotype analysis in the segmentally duplicated DRD5 coding region, Ann Hum Genet 73(3):274-282.

Huang, 2008, Comparative analysis of common CFTR polymorphisms poly-T, TGrepeats and M470V in a healthy Chinese population, World J Gastroenterol 14(12):1925-30.

Husemann, 2009, Phylogenetic Comparative Assembly, Algorithms in Bioinformatics: 9th International Workshop, pp. 145-156, Salzberg & Warnow, Eds. Springer-Verlag, Berlin, Heidelberg.

Hyman, 2010, Multiplex identification of microbes, Appl Env Microbial 76(12):3904-3910.

Illumina, 2010, De Novo assembly using Illumina reads, Technical Note (8 pages).

International Human Genome Sequencing Consortium, 2004, Finishing the euchromatic sequence of the human genome, Nature 431:931-945.

International Preliminary Report on Patentability for PCT/US2010/01293, dated Oct. 28, 2010, (9 pages).

International Preliminary Report on Patentability for WO 2010/126614.

International Search Report and Written Opinion for PCT/US12/29790, dated Jun. 14, 2012 17 pages.

International Search Report and the Written Opinion of the International Searching Authority dated Dec. 23, 2015 for International Application No. PCT/US2015/056037 (13 Pages).

International Search Report and Written Opinion for international application No. PCT/US13/62842 with international filing date Oct. 1, 2013, ISR/WO dated Feb. 4, 2014 (10 pages).

International Search Report and Written Opinion for PCT/US13/61691 dated Jan. 10, 2014 (10 pages).

International Search Report and Written Opinion for PCT/US2013/036575 dated Aug. 12, 2013, 10 pages.

International Search Report and Written Opinion for PCT/US2013/044039 dated Nov. 1, 2013, (15 pages).

International Search Report and Written Opinion for PCT/US2015/056037 dated Dec. 23, 2015; 11 pages.

International Search Report and Written Opinion for WO 2010/126614.

International Search Report and Written Opinion dated Jan. 29, 2015 in counterpart PCT Application No. PCT/US14/61138.

International Search Report and Written Opinion dated Jun. 10, 2013 for related application PCT/US13/33435 with an International filing date of Mar. 22, 2013 (7 pages).

International Search Report and Written Opinion dated Apr. 3, 2012, for International Patent Application No. PCT/US2011/065098, filed Dec. 15, 2011 (8 pages).

International Search Report and Written Opinion dated Aug. 12, 2013, for International Patent Applciation No. PCT/US13/36575, filed Apr. 15, 2013 (9 pages).

International Search Report and Written Opinion dated Dec. 2, 2015, for International Patent Application No. PCT/US2015/049132 with Internaional Filing Date Sep. 9, 2015 (14 pages).

International Search Report and Written Opinion dated Dec. 9, 2014, for International Patent Application No. PCT/US14/28212, filed Mar. 14, 2014 (11 pages).

International Search Report and Written Opinion dated Feb. 25, 2013 for International Patent Application No. PCT/US12/55362.

International Search Report and Written Opinion dated Feb. 4, 2014, for Patent Application No. PCT/US13/62842, filed Oct. 1, 2013 (5 pages).

International Search Report and Written Opinion dated Jan. 7, 2015, for International Patent Application No. PCT/US14/60256, filed Oct. 13, 2014 (9 pages).

International Search Report and Written Opinion dated Jun. 10, 2013, for International Patent Application No. PCT/US13/33435, filed Mar. 22, 2013 (6 pages).

International Search Report and Written Opinion dated Jun. 14, 2012, for International Patent Application No. PCT/US12/29790, filed Mar. 20, 2012 (8 pages).

International Search Report and Written Opinion dated Jun. 28, 2013, for Patent Application No. PCT/US2013/032885, filed Mar. 19, 2013 (9 pages).

International Search Report and Written Opinion dated May 4, 2016, for International patent application No. PCT/US2016/012886 with international filing date Jan. 6, 2015 (7 pages).

International Search Report and Written Opinion dated Nov. 1, 2013, for International Patent Application No. PCT/US2013/044039, filed Jun. 4, 2013 (6 pages).

International Search Report and Written Opinion dated Nov. 16, 2015, for International Application No. PCT/US2015/045247 with International Filing Date Aug. 14, 2015 (10 pages).

International Search Report and Written Opinion dated Jan. 29, 2015, for Patent Application No. PCT/US14/61138, filed Oct. 17, 2014, (11 pages).

International Search Report and Written Opinion dated Jan. 29, 2015, for Patent Application No. PCT/US2014/060056, filed Oct. 10, 2014, (14 pages).

International Search Report and Written Opinion dated Mar. 18, 2015, for Patent Application No. PCT/US14/40516, filed Jun. 2, 2014 (16 pages).

International Search Report and Written Opinion dated May 2, 2016, for International Patent Application No. PCT/US2016/013346, filed Jan. 14, 2016 (7 pages).

International Search Report and Written Opinion dated Oct. 28, 2010, for Patent Application No. PCT/US2010/001293, filed Apr. 30, 2010 (8 pages).

International Search Report and Written Opinion dated Sep. 3, 2014 for International Patent Application No. PCT/US14/27324, filed Mar. 14, 2014, (8 pages).

International Search Report and Written Opinion dated Sep. 2, 2015 for International Patent Application No. PCT/US2015/030366, filed May 12, 2015 (12 pages).

International Search Report and Written Opinion of the International Searching Authority dated Dec. 13, 2016 for International Application No. PCT/US2016/051928 (14 Pages).

International Search Report and Written Opinion of the International Searching Authority dated Jun. 12, 2017 for International Application No. PCT/US2017/016498 (12 Pages).

International Search Report for PCT/US12/55362 dated Feb. 25, 2013, p. 15.

Iqbal, 2012, De novo assembly and genotyping of variants using colored de Bruijn graphs, Nature Genetics 44:226-232.

Isosomppi, 2009, Disease-causing mutations in the CLRN1 gene alter normal CLRN1 protien trafficking to the plasma membrane, Mol Vis 15:1806-1818.

Jaijo, 2010, Microarray-based mutation analysis of 183 Spanish families with Usher syndrome, Invest Ophthalmol Vis Sci 51(3):1311-7.

Jensen, 2001, Orthologs and paralogs—we need to get it right, Genome Biol 2(8):1002-1002.3.

Dahl et al., 2005, Multiplex amplification enabled by selective circularization of large sets of genomic DNA fragments, Nucleic Acids Res 33(8):e71.

Danecek, 2011, The variant call format and VCFtools, Bioinformatics 27(15):2156-2158.

de la Bastide, 2007, Assembling genome DNA sequences with PHRAP, Current Protocols in Bioinformatics 17:11.4.1-11.4.15.

Delcher, 1999, Alignment of whole genomes, Nuc Acids Res 27(11):2369-2376.

den Dunnen, 2003, Mutation Nomenclature, Curr Prot Hum Genet 7.13.1-7.13.8.

Deng et. al., 2012, Supplementary Material, Nature Biotechnology, S1-1-S1-1 1, Retrieved from the Internet on Oct. 24, 2012.

Deng, 2009, Targeted bisulfite sequencing reveals changes in DNA methylation associated with nuclear reprogramming, nature biotechnology 27:353-60 (and supplement).

Deorowicz, 2013, Data compression for sequencing data, Alg for Mole Bio 8:25.

Diep, 2012, Library-free methylation sequencing with bisulfite padlock probes, Nature Methods 9:270-272 (and supplemental information).

(56) References Cited

OTHER PUBLICATIONS

DiGuistini, 2009, De novo sequence assembly of a filamentous fungus using Sanger, 454 and Illumina sequence data, Genome Biology, 10:R94.
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Dong & Yu, 2011, Mutation surveyor: An in silico tool for sequencing analysis, Methods Mol Biol 760:223-37.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12): e1000589.
Ericsson, 2008, A dual-tag microarray platform for high-performance nucleic acid and protein analyses, Nucl Acids Res 36:e45.
Examination Report from the European Patent Office for EP 10770071.8 dated Jul. 16, 2013, (5 pages).
Extended European Search Report for Application No. 12765217.0 dated Aug. 26, 2014, (5 pages).
Extended European Search Report for EP 15844985.0 dated May 15, 2018 (10 pages).
Extended European Search Report dated Nov. 11, 2015, for EP Application 13772357.3 (8 pages).
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014.
Fitch, 1970, Distinguishing homologs from analogous proteins, Syst Biol 19(2):99-113.
Flaschker et al., 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke et al., 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan (106 pages).
Goto, 2010, BioRuby: bioinformatics software for the Ruby programming language, Bioinformatics 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nuel Acids Res 19(11):3019-3025.
Gustincich et al., 1991, A fast method for high-quality genomic DNA extraction from whole human blood, BioTechniques 11(3):298-302.
Gut, 2995, A procedure for selective DNA alkylation and detection by mass spectrometry, Nucl Acids Res 23(8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harper, 2011, Preimplantation genetic diagnosis: State of the ART 2011, Human Genet 131(2):175-186.
Harris, 2006, Defects can increase the melting temperature of DNA-nanoparticle assemblies, J Phys Chem B 110(33):16393-6.
Harris, 2008, Helicos True Single Molecule Sequencing (tSMS) Science 320:106-109.
Harris, 2008, Single-molecule DNA sequencing of a viral genome, Science 320(5872):106-9.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hill, 1991, The use of pH indicators to identify suitable environments for freezing samples in aqueous and mixed aqueous/nonaqueous solutions, Anal Biochem 192(2):358-361.
Adey, 2010, Rapid, low-input, low-bias construction of shotgun fragment libraries by high-density in vitro transposition, Genome Biol 11:R119.
Ageno, 1969, The alkaline denaturation of DNA, Biophys J 9(11):1281-1311.
Agrawal, 1990, Site-specific functionalization of oligodeoxynucleotides for non-radioactive labelling, Tetrahedron Let 31:1543-1546.
Akhras, 2007, Connector Inversion Probe Technology: A Powerful OnePrimer Multiplex DNA Amplification System for Numerous Scientific Applications PLOS ONE 2(9):e915.
Alazard, 2002, Sequencing of production-scale synthetic oligonucleotides by enriching for coupling failures using matrix-assisted laser desorption/ionization time-of-flight mass spectrometry, Anal Biochem 301:57-64.
Alazard 2006, Sequencing oligonucleotides by enrichment of coupling failures using matrix-assisted laser desorption/ionization time-of-flight mass spectrometry, Curr Protoc Nucleic Acid Chem, Chapter 10, Unit 10:1-7.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401.
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.

(56) References Cited

OTHER PUBLICATIONS

Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3(65ra4).
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bickle, 1993, Biology of DNA Restriction, Microbiol Rev 57(2):434-50.
Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brinkman, 2004, Splice Variants as Cancer Biomarkers, Clin Biochem 37:584.
Brown et al., 1979, Chemical synthesis and cloning of a tyrosine tRNA gene, Methods Enzymol 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA.
Campbell, 1992, Detection of Chlamydia pneumoniae by polymerase chain reaction, J Clin Microbiol 30(2):434-439.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
CDC, 2011 Assisted Reproductive Technology: Fertility Clinic Success Rates Report.
Challis, 2012, An integrative variant analysis suite for whole exome next-generation sequencing data, BMC Informatics 13(8):1-12.
Chan, 2011, Natural and engineered nicking endonucleases—from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013.

Chevreux, 1999, Genome sequence assembly using trace signals and additional sequence information, Proc GCB 99:45-56.
Chirgwin et al., 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Ciotti, 2004, Triplet repeat prmied PCR (TP PCR) in molecular diagnostic testing for Friedrich ataxia, J Mol Diag 6(4):285-9.
Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.
Cronin, 1996, Cystic Fibrosis Mutation Detection by Hybridization to Light-Generated DNA Probe Array Human Mutation 7:244.
Wang et al., 2005, Allele quantification using molecular inversion probes (MIP), Nucleic Acids Research 33(21):e183.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988.
Watson et al., 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial tRNAphe Variant m.593T.Ca Synergistically Pathogenic Mutation in Chinese LHON Families with m.11778G.A? PLoS ONE 6(10):e26511.
Zhao, 2009, PGA4genomics for comparative genome assembly based on genetic algorithm optimization, Genomics 94(4):284-6.

(56) References Cited

OTHER PUBLICATIONS

Zheng, 2011, iAssembler: a package for de novo assembly of Roche-454/Sanger transcriptome sequences, BMC Bioinformatics 12:453.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Saihan, 2009, Update on Usher syndrome, Cur Op Neurology 22:19-27.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1988, Isolation of differentially expressed genes, Methods Enzymol 152:423-432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, 2010, A window into third-generation sequencing, Human Mol Genet 19(R2):R227-40.
Schatz et al., 2010, Assembly of large genomes using second-generation sequencing, Genome Res., 20:1165-1173.
Schiffman, 2009, Molecular inversion probes reveal patterns of 9p21 deletion and copy number aberrations in childhood leukemia, Cancer Genetics and Cytogenetics 193:9-18.
Zhou, 2014, Bias from removing read duplication in ultra-deep sequencing experiments, Bioinformatics 30(8):1073-1080.
Zimmerman, 2010, A novel custom resequencing array for dilated cardiomyopathy, Gen Med 12(5):268-78.
Zuckerman, 1987, Efficient methods for attachment of thiol specific probes to the 3'-ends of synthetic oligodeoxyribonucleotides, Nucl Acid Res 15(13):5305-5321.
Schneeberger, 2011, Reference-guided assembly of four diverse *Arabidopsis thaliana* genomes, PNAS 108(25):10249-10254.
Schoolcraft, 2010, Clinical application of comprehensive chromosomal screening at the blastocyst stage, Fert Steril 94(5):1700-1706.
Schouten, 2002, Relative Quantification of 40 Nucleic Acid Sequences by Multiplex Ligation-Dependent Probe Amplification, Nucle Acids Res 30 (12):257.
Schrijver, 2005, Diagnostic testing by CFTR gene mutation analysis in a large group of Hispanics, J Mol Diag 7(2):289-299.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31.
Smirnov, 1996, Sequencing oligonucleotides by exonuclease digestion and delayed extraction matrix-assisted laser desorption ionization time-of-flight mass spectrometry, Anal Biochem 238:19-25.
Smith, 1985, The synthesis of oligonucleotides containing an aliphatic amino group at the 5' terminus: synthesis of fluorescent DNA primers for use in DNA sequence analysis, Nucl. Acid Res., 13:2399-2412.
Smith, 2010, Highly-multiplexed barcode sequencing: an efficient method for parallel analysis of pooled samples, Nucleic Acids Research 38(13):e142 (8 pages).
Soni, 2007, Progress toward ultrafast DNA sequencing using solid-state nanopores, Clin Chem 53(11):1996-2001.
Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30):1-9.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tkachuk, 1990, Detection of bcr-abl Fusion in Chronic Myelogeneous Leukemia by in Situ Hybridization, Science 250:559.
Tobler, 2005, The SNPlex Genotyping System: A Flexible and Scalable Platform for SNP Genotyping, J Biomol Tech 16(4):398.
Tokino, 1996, Characterization of the human p57 KIP2 gene: alternative splicing, insertion/deletion polymorphisms in VNTR sequences in the coding region, and mutational analysis, Human Genetics 96:625-31.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013.
Umbarger, 2014, Next-generation carrier screening, Gen Med 16(2):132-140.
Veeneman, 2012, Oculus: faster sequence alignment by streaming read compression, BMC Bioinformatics 13:297.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Miner, 2004, Molecular barcodes detect redundancy and contamination in hairpin-bisulfite PCR, Nucl Acids Res 32(17):e135.
Minton, 2011, Mutation Surveyor: software for DNA sequence analysis, Meth Mol Biol 688:143-53.

(56) References Cited

OTHER PUBLICATIONS

Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, DELIMINATE—a fast and efficient methods for loss-less compression of genomice sequences, Bioinformatics 28(19):2527-2529.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment—the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen et al., 1999, Peptide Nucleic Acids, Protocols and Applications (Norfolk: Horizon Scientific Press, 1-19).
Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.

Ostrer, 2001, A genetic profile of contemporary Jewish populations, Nat Rev Genet 2(11):891-8.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea et al., 2003, TIGR Gene indices clustering tools (TGICL): a software system for fast clustering of large EST datasets, Bioinformatics 19(5):651-52.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplification of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed. (72 pages).
Quail et al., 2010, DNA: Mechanical Breakage, Encyclopedia of Life Sciences 2010.
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS ONE 3:e3373.
Roberts, 1980, Restriction and modification enzymes and their recognition sequences, Nucleic Acids Res 8(1):r63-r80.
Robinson et al., 2013, Graph Databases, O'Reilly Media, Inc., Sebastopol, CA (223 pages).
Rodriguez, 2010, Constructions from Dots and Lines, Bull Am Soc Inf Sci Tech 36(6):35-41.
Rosendahl et al., 2013, CFTR, SPINK1, CTRC and PRSS1 variants in chronic pancreatitis: is the role of mutated CFTR overestimated?, Gut 62:582-592.

\* cited by examiner

PROCESS CONTROL FOR INCREASED ROBUSTNESS OF GENETIC ASSAYS

CROSS-REFERENCE TO RELATED APPLICATION

This application claims the benefit of and priority to U.S. Provisional Patent Application Ser. No. 62/054,725, filed Sep. 24, 2014, the contents of which are incorporated by reference herein in their entirety.

FIELD OF THE INVENTION

The invention generally relates to compositions and methods for processing a biological sample. More specifically, it relates to compositions and methods for analyzing a sample in a preimplantation genetic screening assay.

BACKGROUND

Preimplantation genetic screening (PGS) is a procedure in which one or more cells are biopsied from an embryo and analyzed to determine the karyotype of the embryo. The biopsy typically is performed by an embryologist, who places the cell(s) in a tube with 2-3 ul of liquid before freezing and delivering to a laboratory for testing. The laboratory receives the frozen liquid containing the biopsied cell(s), and performs a lysis procedure to liberate the nucleic acid. The lysis can be performed in several different ways, but the most common technique uses an alkaline solution, optionally in the presence of elevated temperature, to lyse the cell(s) and potentially denature and/or shear the nucleic acid for downstream analysis.

By profiling embryos for certain genetic disorders, a prospective parent may select embryos that lack the disorder, have an increased chance of successful pregnancy, have a lower predisposition to cancer, and a variety of other considerations. Preimplantation genetic diagnosis is used to select desired oocytes or embryos from a group of oocytes or fertilized embryos, some of which may be at risk, rather than assaying for a specific disease or condition. Preimplantation genetic screening can also be used to select embryos that have a euploid chromosome complement (22 pairs of autosomes and 2 sex chromosomes), or that lack finer-scale genomic rearrangements including translocations or sub-chromosomal gains or losses, thereby increasing the chance that the embryo will successfully implant, develop to term, and result in a healthy live birth, and decreasing the potential desire for selective pregnancy termination.

Preimplantation genetic screening may involve removing multiple eggs from a donor, fertilizing them to produce embryos, analyzing the embryos, and selecting an embryo that meets certain desired characteristics. To analyze a preimplanted embryo or blastocyst, only a small amount of cellular material can generally be biopsied. Because the embryo or blastocyst may have only a few dozen cells altogether, a PGS assay may involve biopsying only a single cell. Generally, the cell or cells are biopsied and analyzed to determine the karyotype of the embryo.

SUMMARY

The present disclosure provides compositions and related methods for processing a cellular sample. Specifically, methods of the invention involve utilizing an optical indicator in order to determine whether a liquid sample comprising cells is frozen prior to shipment for laboratory testing, and for monitoring and ensuring the integrity of the process in the laboratory that lyses the cells to free their nucleic acid for downstream analysis. Moreover, it has been discovered that certain indicators are also useful in stabilizing the sample as well as monitoring pH.

In one embodiment, a cellular sample is obtained by biopsy and placed in an appropriate buffer or collection storage fluid. The indicator, described more specifically below, is added and the sample is frozen. Alternately, a cellular sample can be obtained by biopsy and placed into an appropriate storage or collection fluid that already contains the indicator. A color change in the indicator is used to determine that the sample is frozen and is sufficient for delivery to a laboratory. The laboratory may be on the same premises that obtains and freezes the sample or may be remote (i.e., the frozen sample can simply be stored prior to delivery to laboratory personnel for testing). Alternatively, a change in electrical conductivity in the sample is used to monitor the indicator.

A particularly useful mode of practicing the invention is in the context of preimplantation genetic screening in which the quality and position of the frozen sample is critical prior to processing for genetic analysis. Biopsied embryonic material is placed in a collection tube with a collection buffer. An indicator is then added to the collection tube. Any indicator that is useful in determining whether the sample has been prepared properly may be used. However, a particularly useful indicator in the context of PGS is cresol red, or another triarylmethane dye. Cresol red is an example of a halochromic chromophore that changes color within the visible spectrum in response to changes in pH. The presence of cresol red aids in visualizing the small aliquot of liquid used in PGS, thereby allowing for improved monitoring of liquid placement and freezing, as well as monitoring fine pH adjustments. After the initial collection of sample and the addition of cresol red, the sample is often optionally frozen and shipped to another laboratory for further analysis. Proper freezing and thawing of the sample are necessary for maintaining the integrity of the cellular sample. Cresol red has been discovered to change color in response to freezing, and so its presence in the tube is useful for alerting a clinician handling the sample whether it has been properly frozen or thawed.

After thawing, the sample may be lysed by adding an alkaline lysis solution to the tube. The clinician performing the method can monitor the liquid for the appropriate color change and adjust the pH by titrating with an acid or base, as needed, to achieve the proper range for the lysis step. After lysis, the pH is neutralized by adding a neutralization solution and again monitoring for an appropriate color change, which signals that the sample has achieved the proper range. The pH can again be fine-tuned as necessary to ensure the appropriate neutral pH for subsequent downstream analysis.

The presence of cresol red or another pH indicator in the liquid mixture allows a clinician to ensure that: a) the liquid is in the bottom of the tube before freezing; b) the liquid is frozen before the tubes are shipped by the embryologist; c) the liquid is frozen when received by the laboratory; d) a volume of alkaline solution sufficient to increase pH is added to the tube; and e) a volume of acid sufficient to neutralize pH is added to the tube.

In alternative embodiments of the method, the pH indicator can be added at any step. Because a pH indicator such as cresol red provides multiple benefits at various steps throughout the method (i.e., visualizing the liquid before freezing, ensuring proper freezing and thawing, and monitoring subtle pH changes), it is beneficial to add it early in the procedure. However, those of skill in the art will understand that some assays may not require early addition of the pH indicator, such as assays that do not involve freezing, for example. Also, some assays that have other limitations, such as where the addition of pH indicator would interfere with an early step in the protocol, would also benefit from a later addition of the indicator.

After each step performed in the laboratory, the color change of the pH indicator can be monitored by eye. Alternatively it can be monitored automatically by a system including a camera controlled by computer software capable of determining the precise color of the solution, and therefore the precise pH. The computer software can flag any samples that are not at the correct pH for intervention to ensure that the solution is brought to the correct pH before downstream analytical steps are performed. If a sample has an incorrect pH, it can be adjusted by adding an appropriate amount of acid or base, either by automated means or manually by the clinician.

The method can be performed using cresol red, any other triarylmethane dye, or any other pH indicator that changes color in response to changes in pH, as long as the pH indicator is compatible with downstream analytical steps. For example, a pH indicator that is known to interfere with the activity of Taq polymerase would not be useful for an assay that required Taq-based PCR after lysis and neutralization.

DETAILED DESCRIPTION

The present disclosure describes methods of processing a biological sample. The method includes contacting the sample with an indicator that changes color in response to changes in pH. The presence of a pH indicator, such as cresol red, provides the benefit of improved visualization of the sample, verification that the sample is properly frozen and thawed, and increased precision in pH adjustments during the assay, among other benefits.

The method is particularly useful for preimplantation genetic screening (PGS). PGS assays generally involve small samples in small volumes of liquid, which must be frozen and thawed prior to analysis. Additionally, PGS protocols require various pH adjustments that must be precise in order to maintain the efficacy of the assay. The addition of a pH indicator such as cresol red to the liquid mixture allows a clinician to ensure that: a) the liquid is in the bottom of the tube before freezing; b) the liquid is frozen before the tubes are shipped by the embryologist; c) the liquid is frozen when received by the laboratory; d) a volume of alkaline solution sufficient to increase pH is added to the tube; and e) a volume of acid sufficient to neutralize pH is added to the tube.

While the methods described herein are particularly useful for PGS analysis, they can also be used for other assays of biological materials. In addition to assaying an embryonic sample, the methods can be used to analyze a buccal sample, a blood sample, an amniotic fluid sample, a cervical sample, an ocular sample, or any other sample comprising cells or cellular materials including nucleic acid. The methods described herein can be adapted to any assay known in the art that requires one or more steps involving a change in pH of the sample or reaction mixture.

Although a preferred embodiment of the invention involves the use of cresol red, the method can be performed using another triarylmethane dye. Triarylmethane dyes are synthetic organic compounds containing triphenylmethane backbones, and presenting intense colors in the visual spectrum. Many react to changes in pH, and are therefore useful as pH indicators. Any other pH indicator can be used with methods of the invention, as long as it changes color or otherwise reacts in response to changes in pH, and it is compatible with downstream analytical steps. For example, a pH indicator that is known to interfere with the activity of Taq polymerase would not be useful for an assay that involved Taq-based PCR downstream of the lysis and neutralization steps.

Figure 1:
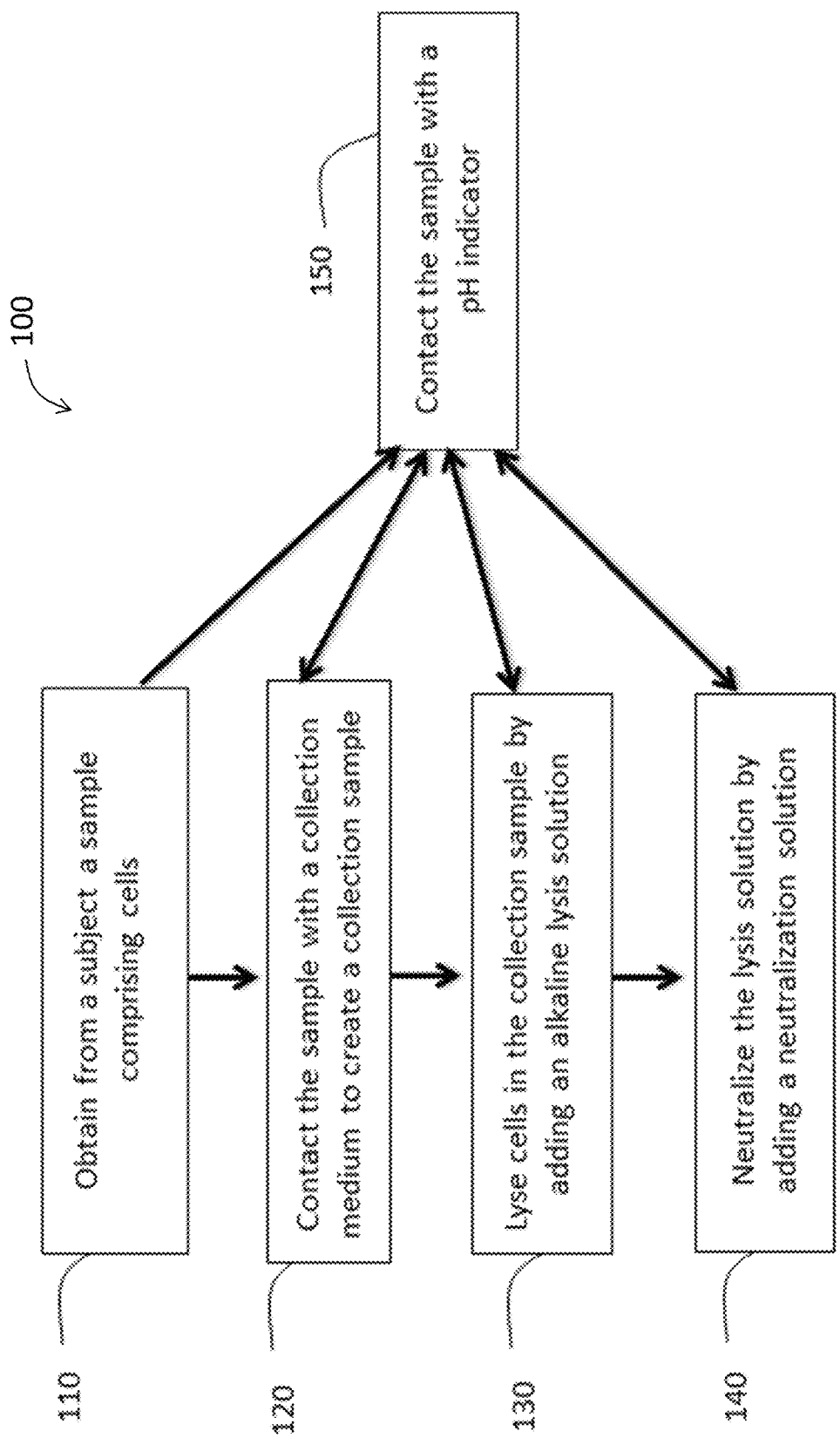
FIG. 1 shows the steps of a method for processing a biological sample.

FIG. 1 is a flowchart 100 depicting a series of steps in a preferred embodiment of the invention. The flowchart 100 shows steps for processing a biological sample by methods of the present disclosure. In step 110, a sample comprising cells is obtained from a subject. The sample can be comprised of one or more cells biopsied from an embryo or oocyte of a subject. After the sample is collected it is contacted with a collection medium in step 120. The collection medium can be a buffer, an alcohol, a preservative medium, or any other such medium that would be known to a person skilled in the art. Often for PGS analysis, the volume of collection medium is very small. It can be, for example, 1 μl or less. The volume can also be about 2 μl, 3 μl, 4 μl, 5 μl, 10 μl, 20 μl, 50 μl, 100 μl, or more, depending on the needs of the assay.

After step 120, the sample may be frozen and shipped to another lab to perform the subsequent steps of the procedure. Alternatively, all steps can be performed in a single lab, obviating the need to freeze and thaw the sample. In embodiments of the invention that involve freezing the collection sample, the collection sample is thawed prior to performing step 130. In step 130, the cells in the collection sample are lysed by the addition of an alkaline lysis solution to the mixture. In other embodiments of the method, the cells are lysed using other techniques, such as mechanical shearing, osmotic lysing, chemical denaturing, centrifuging, sonicating, freeze-thawing, or other techniques known in the art.

When lysis is performed using an alkaline solution, such as in step 130, optionally the solution can be exposed to elevated temperatures to further catalyze the lysis process. In step 130 the cell or cells in the mixture are lysed and nucleic acids therein may also be denatured or sheared, preparing them for downstream analysis.

Following step 130, the solution is neutralized in step 140 by adding a neutralization solution. Generally the neutralization solution will be acidic, to neutralize the alkaline lysis solution. The lysis step 130 and the neutralizing step 140 both require precision to achieve proper pH levels. Imprecision in the pipetted volume of either the lysis reagent or the neutralizing reagent will result in a suboptimal pH. If the pH after step 140 is not neutral, for example, the downstream steps may be impeded, which may lead to assay failure.

For that reason, among others, a pH indicator is added in step 150. A pH indicator such as cresol red is useful with methods of the invention. Cresol red is a halochromic chromophore that changes color within the visible spectrum in response to changes in pH. It appears yellow below pH 7.2, red until pH 8.8, and violet above pH 8.8. The color change of the pH indicator can be monitored by eye, or it can be monitored automatically by a system including a camera controlled by computer software capable of determining the precise color of the solution, and therefore the precise pH. The computer software can flag any samples that are not at the correct pH, and a clinician can intervene to ensure that the solution is brought to the optimal pH before downstream analytical steps are performed. That intervention can also be automated, whereby the computer system triggers a pH adjustment in response to identifying an incorrect pH. The pH adjustments, whether performed manually by a lab technician or automatically by a computer system, can be achieved by adding an appropriate amount of acid or base as necessary.

In various embodiments of FIG. 1, step 150 can occur immediately downstream of any of steps 110-140. Methods of the invention include the step of contacting the sample with an indicator 150 immediately after step 110, step 120, step 130, or step 140. In other embodiments, step 150 is performed simultaneously with steps 120, 130, 140, or 150.

The addition of a pH indicator such as cresol red has advantages at various stages of the method. The presence of cresol red or another compatible pH indicator helps monitor the sample throughout a procedure that requires multiple fine pH adjustments. Further, as discussed above, the sample is often frozen and shipped to another laboratory for further analysis after the initial collection of sample. That means that proper freezing and thawing of the sample are necessary for maintaining the integrity of the cellular sample. It has been discovered that cresol red changes color in response to freezing and thawing, and so its presence in the sample mixture at steps 120, 130, and 140 help to verify that the sample has been properly handled. Additionally, cresol red allows easier visualization of small amounts of liquid in the sample tube. Therefore, the presence of cresol red is especially useful in PGS and other similar assays, where the volume is small and the clinician must ensure that the sample is at the bottom of the tube prior to freezing.

In addition to cresol red, other pH indicators that are useful in other embodiments of the disclosed invention are gentian violet (Methyl violet 10B), malachite green, thymol blue, methyl yellow, bromophenol blue, congo red, methyl orange, bromocresol green, methyl red, azolitmin, bromocresol purple, bromothymol blue, phenol red, neutral red, naphtholphthalein, cresolphthalein, phenolphthalein, thymolphthalein, alizarine yellow R, and any other common laboratory pH indicator known in the art.

Figure 2A:
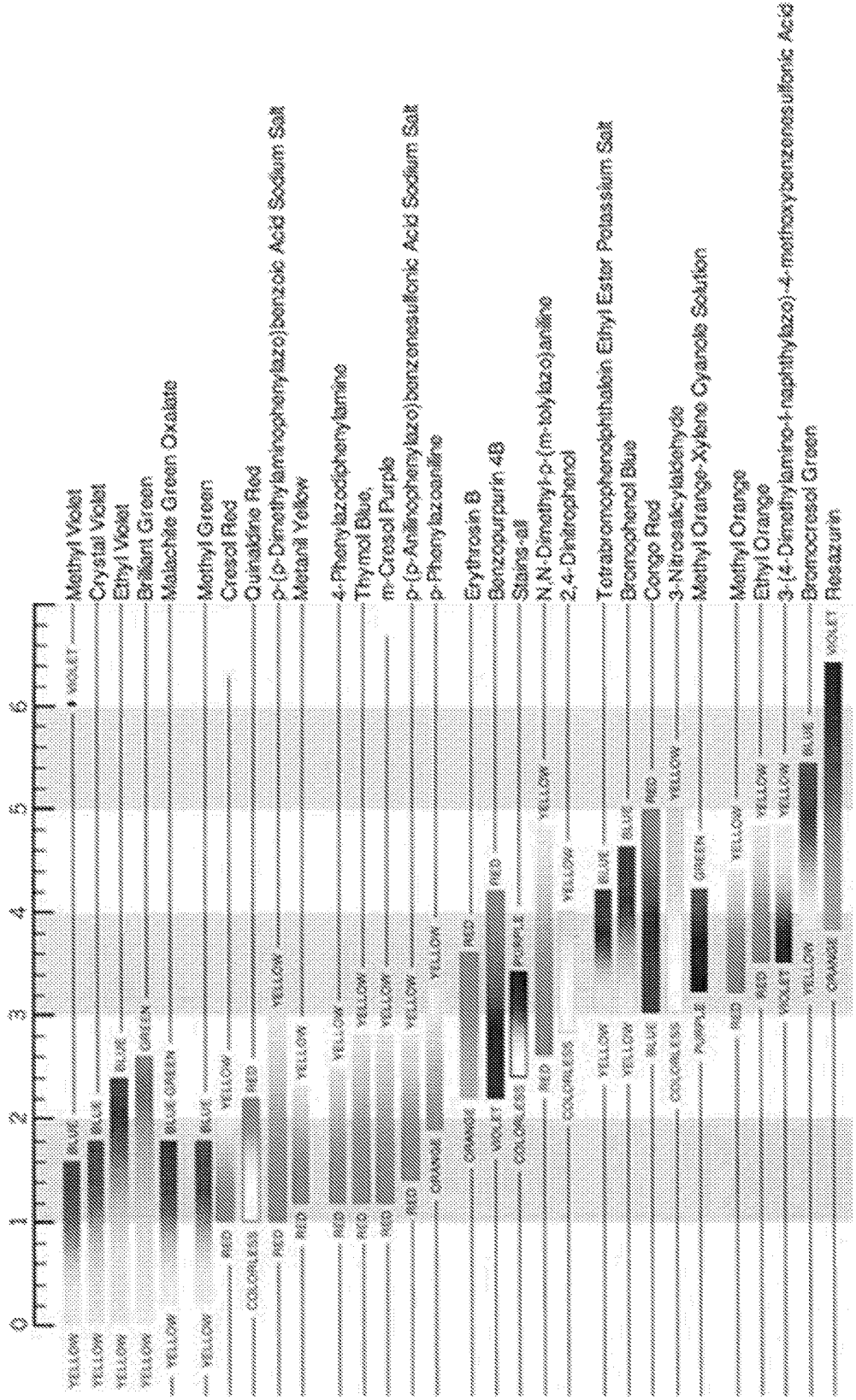
FIGS. 2A and 2B show a variety of pH indicators and their characteristic color ranges.
Figure 2B:
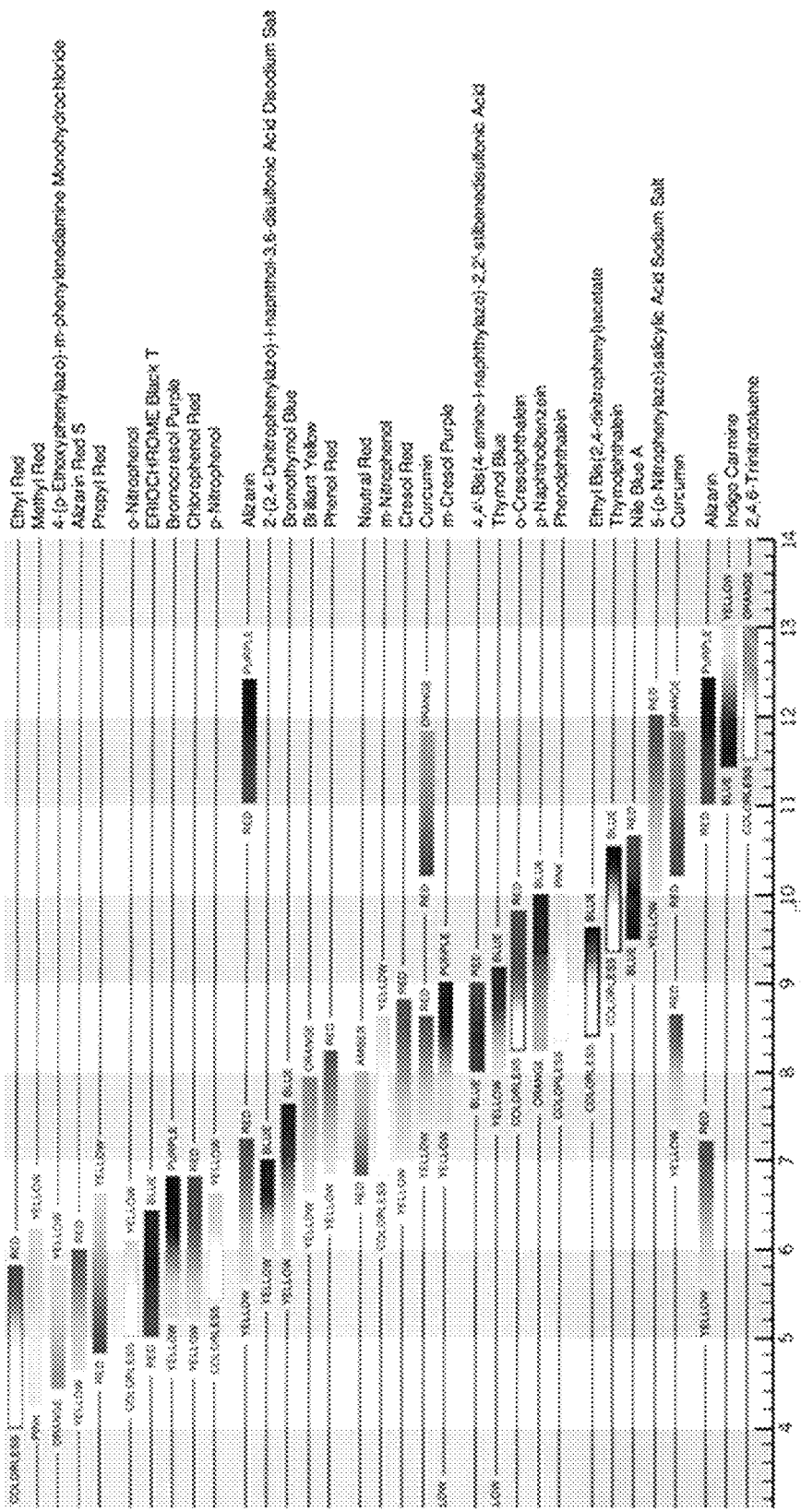

FIGS. 2A-B show a list of several pH indicators that can be used with the invention, along with the characteristic color changes for each indicator at different pH levels. As shown in FIGS. 2A-B, several indicators have overlapping ranges for most levels of pH. That means that for a given assay requiring a specific pH, numerous pH indicators could be used. For the PGS assay described above, indicators such as neutral red and phenol red have similar ranges as cresol red, and therefore could be substituted. For assays involving different pH requirements, a pH indicator can be selected that has a suitable range that would allow an observer to differentiate between subtle pH variances as needed.

In addition to those listed in FIGS. 2A-B, other pH indicators include anthocyanins, litmus, and hydrangea flowers. Additionally, fluorescent dyes can be used as direct pH indicators, as fluorescence is a function of pH. Nucleic acid reporter molecules, which denature at pH extremes and renature or otherwise change structural formation at neutral pH, can also be used. These can be coupled with flourophore/quencher pair, a FRET pair, or mixed with intercalating dye for structural readout. Protein reporter molecules, which change conformation as a function of pH, can be used in a similar manner as can pH sensitive fluorescent proteins (see, e.g., Kneen, 1998, "Green fluorescent protein as a noninvasive intracellular pH indicator," *Biophys J.* 74(3): 1591-99; Miesenböck, 1998, "Visualizing secretion and synaptic transmission with pH-sensitive green fluorescent proteins," *Nature* 394(6689):192-95; and Llopis, 1998, "Measurement of cytosolic, mitochondrial, and Golgi pH in single living cells with green fluorescent proteins," *Proc. Natl. Acad. Sci. U.S.A.* 95(12):6803-08).

Additionally, pH can be measured electronically using a pH meter. Electronic pH meters are available, such as the Hach HQ440D Benchtop Meter, available from Hach Company (Loveland, Col.). Also available are miniaturized pH meters such as Ion Torrent or ion-sensitive field-effect transistors, which detect ion concentration changes in a solution and respond with a changed current through a transistor. As discussed above, in all cases, the selected pH measurement technique should be compatible with downstream analytical steps. Some halochromic chromophores, such as bromophenol blue, for example, are known to interfere with the normal activity of Taq polymerase, and so would not be an optimal choice if a Taq-based PCR were to be performed on the nucleic acid after lysis and neutralization.

The disclosure additionally provides a composition of matter, the composition comprising a sample comprising one or more cells, a collection medium, an alkaline lysis solution, a neutralization solution, and a pH indicator. The composition provides a reaction mixture for PGS analysis that is more stable and that is easier to adjust for desired pH levels than compositions of the prior art. The composition can comprise a sample that has been biopsied from an embryo. Alternatively the sample can be a buccal sample, a blood sample, an amniotic fluid sample, a cervical sample, an ocular sample, or any other sample comprising cells or cellular materials including nucleic acid. The collection medium can be a buffer, an alcohol, or a preservative medium, or any other similar medium known in the art. The neutralization solution comprises any solution that neutralizes the pH of the lysis solution. Therefore, when the lysis solution is alkaline, the neutralization solution is acidic. The pH indicator can be cresol red, or any other pH indicator listed in FIGS. 2A-B or otherwise known in the art. The composition can be produced in conjunction with the methods described herein.

As discussed above, the color changes of the pH indicator can be observed by an automated mechanism such as a camera connected to a computer. As one skilled in the art would recognize as necessary or best-suited for performance of the methods of the invention, computer system or machines of the invention include one or more processors (e.g., a central processing unit (CPU) a graphics processing unit (GPU) or both), a main memory and a static memory, which communicate with each other via a bus.

Figure 3:
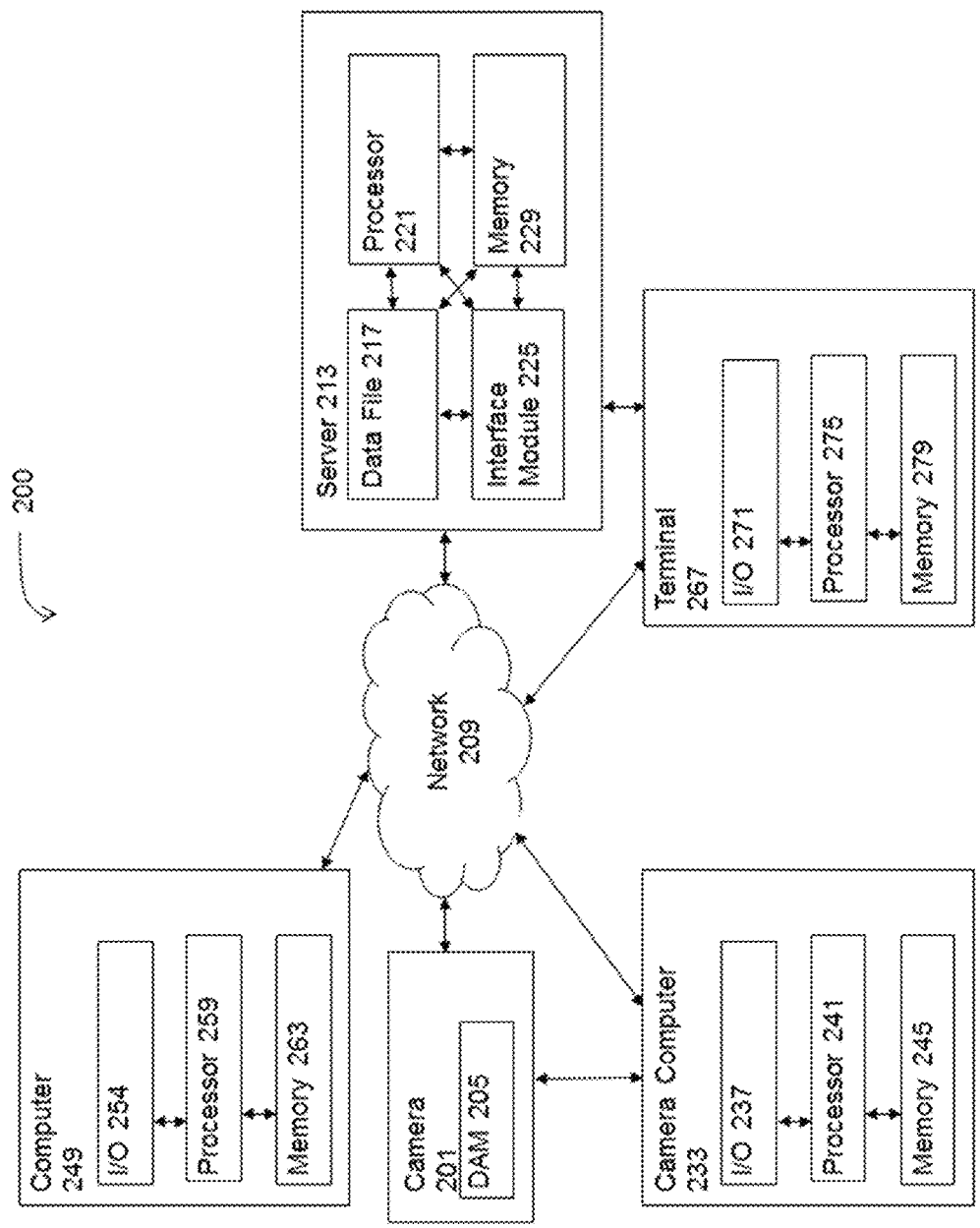
FIG. 3 shows a system configured to identify color changes in a halochromic chromophore using a camera.

In an exemplary embodiment shown in FIG. 3, system 200 can include a camera 201 with data acquisition module 205 to obtain sequence read data. Camera 201 may optionally include or be operably coupled to its own, e.g., dedicated, camera computer 233 (including an input/output mechanism 237, one or more of processor 241 and memory 245). Additionally or alternatively, camera 201 may be operably coupled to a server 213 or computer 249 (e.g., laptop, desktop, or tablet) via network 209. Computer 249 includes one or more processor 259 and memory 263 as well as an input/output mechanism 254. Where methods of the invention employ a client/server architecture, steps of methods of the invention may be performed using server 213, which includes one or more of processor 221 and memory 229, capable of obtaining data, instructions, etc., or providing results via interface module 225 or providing results as a file 217. Server 213 may be engaged over network 209 through computer 249 or terminal 267, or server 213 may be directly connected to terminal 267, including one or more processor 275 and memory 279, as well as input/output mechanism 271.

System 200 or machines according to the invention may further include, for any of I/O 249, 237, or 271 a video display unit (e.g., a liquid crystal display (LCD) or a cathode ray tube (CRT)). Computer systems or machines according to the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 245, 279, or 229 according to the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media.

The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories (e.g., subscriber identity module (SIM) card, secure digital card (SD card), micro SD card, or solid-state drive (SSD)), optical and magnetic media, and any other tangible storage media.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for processing a biological sample, the method comprising:
   obtaining a sample comprising at least one cell biopsied from an embryo in a solution of 2-3 µl of liquid;
   contacting the sample with an indicator dye comprising cresol red that provides a visual indication that the sample is frozen and within a specific, pre-defined pH range;
   exposing the sample to a freezing temperature;
   determining based on the visual indication that the sample is frozen; and
   performing a preimplantation genetic screening procedure comprising:
      using a camera controlled by computer software to evaluate a color of the sample;
      confirming with the computer software that the color indicates that the sample remains frozen;
      contacting the sample with an alkaline lysis solution followed by contacting the sample with an acid to achieve a neutral pH;
      using the camera and the computer software to evaluate a color of the sample and confirm that the sample has a neutral pH; and
      analyzing a karyotype of the at least one biopsied cell in the sample.

2. The method of claim 1, further comprising:
   assessing said indicator in order to determine if the pH range is appropriate; and
   delivering the sample to a laboratory if said indicator indicates that the sample is frozen.

3. The method of claim 1, further comprising the step of assessing said indicator in order to determine a position of said cells in a vial containing the sample.

4. The method of claim 1, wherein the alkaline lysis solution contains said indicator; and wherein the acid contains said indicator.

5. The method of claim 2, wherein said assessing step is performed by observing a color change in the sample.

6. The method of claim 5, wherein color change is monitored by automatic means, wherein the automatic means comprises a camera.

7. The method of claim 2, wherein said assessing step is performed by monitoring electrical conductivity in the sample.

* * * * *